US012625092B2

(12) United States Patent
Zhang et al.

(10) Patent No.: US 12,625,092 B2
(45) Date of Patent: May 12, 2026

(54) CORRECTION METHOD FOR SCATTER SIGNAL CAUSED BY WEDGE FILTER

(71) Applicant: Siemens Shanghai Medical Equipment Ltd., Shanghai (CN)

(72) Inventors: Guo Qing Zhang, Shanghai (CN); Yang Wang, Shanghai (CN); Wen Hao Chen, Shanghai (CN); Tao Tao Li, Shanghai (CN); Yi Tian, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 230 days.

(21) Appl. No.: 18/696,435

(22) PCT Filed: Aug. 24, 2022

(86) PCT No.: PCT/CN2022/114507
§ 371 (c)(1),
(2) Date: Mar. 28, 2024

(87) PCT Pub. No.: WO2023/051107
PCT Pub. Date: Apr. 6, 2023

(65) Prior Publication Data
US 2024/0385128 A1    Nov. 21, 2024

(30) Foreign Application Priority Data

Sep. 30, 2021    (CN) .......................... 202111162044.0

(51) Int. Cl.
*G01N 23/046*        (2018.01)
*A61B 6/58*          (2024.01)
(Continued)

(52) U.S. Cl.
CPC ............ *G01N 23/046* (2013.01); *A61B 6/032* (2013.01); *A61B 6/06* (2013.01); *A61B 6/583* (2013.01)

(58) Field of Classification Search
CPC ........ G01N 23/046; A61B 6/032; A61B 6/06; A61B 6/583; A61B 6/4291; A61B 6/4035;
(Continued)

(56) References Cited

U.S. PATENT DOCUMENTS

2007/0086561 A1    4/2007  Bruder et al.
2011/0249879 A1*  10/2011  Wu ....................... G06T 11/005
                                                                  382/131
(Continued)

FOREIGN PATENT DOCUMENTS

CN    101028195 A    9/2007
CN    108606805 A    10/2018
(Continued)

OTHER PUBLICATIONS

Zhang Guoqing et al: "Biomedical Physics & Engineering Express Correction of Bowtie filter induced scatter signals based on air scan data and object scan data", Biomed. Phys. Eng. Express, Jun. 28, 2022 (Jun. 28, 2022), pp. 1-10, XP055983143, Retrieved from the Internet: URL:https://iopscience.iop.org/article/10. 1088/2057-1976/ ac5d0c/pdf {retrieved on Nov. 19, 2022].
(Continued)

*Primary Examiner* — Courtney D Thomas
(74) *Attorney, Agent, or Firm* — Banner & Witcoff, Ltd.

(57)                ABSTRACT
A correction method for a scatter signal caused by a wedge filter includes: S10: performing an air scan by using CT equipment, and calculating a relative intensity $W_{air}$ of a scatter signal caused by a wedge filter in the air scan according to an air scan result, S20: performing an object
(Continued)

scan on a plurality of experimental objects by using the CT equipment, and calculating theoretical scatter signal intensities $W_{theo}$ of the experimental objects in the object scan in combination with the result of S10, S30: fitting $W_{theo}$ of the experimental objects in the object scan and scatter signal intensity estimations $W_{act}$ of the experimental objects in the object scan, and S40: correcting the scan results according to a difference between a scatter signal intensity estimation $W_{act}$ of an actual object in the object scan and a theoretical scatter signal intensity $W_{theo}$ of the actual object in the object scan.

7 Claims, 6 Drawing Sheets

(51) Int. Cl.
A61B 6/03         (2006.01)
A61B 6/06         (2006.01)

(58) Field of Classification Search
CPC ................ A61B 6/5282; G06T 11/005; G06T 2211/448; G06T 2211/452
See application file for complete search history.

(56) References Cited

U.S. PATENT DOCUMENTS

| | | |
|---|---|---|
| 2013/0058450 A1 | 3/2013 | Liu et al. |
| 2017/0148192 A1 | 5/2017 | Bauer et al. |
| 2019/0197740 A1 | 6/2019 | Lu et al. |

FOREIGN PATENT DOCUMENTS

| | | |
|---|---|---|
| CN | 111096761 A | 5/2020 |
| DE | 102011089643 A1 | 6/2013 |
| JP | H1033520 A | 2/1998 |

OTHER PUBLICATIONS

Nov. 28, 2022 (PCT) International Search Report and Written Opinion—App. PCT/CN2022/114507.
Journal of Biomedical Engineering, Issue 02; Jun. 25, 1997 ; Zhensheng Deng, Daoping Ni, Dazong Jiang, Zhenghai Zhao, Feng Xiao, Lijie Xu. A Method for Correcting X-ray Image Scatter Using Deconvolution ; pp. 137-143.

* cited by examiner

Figure 1:
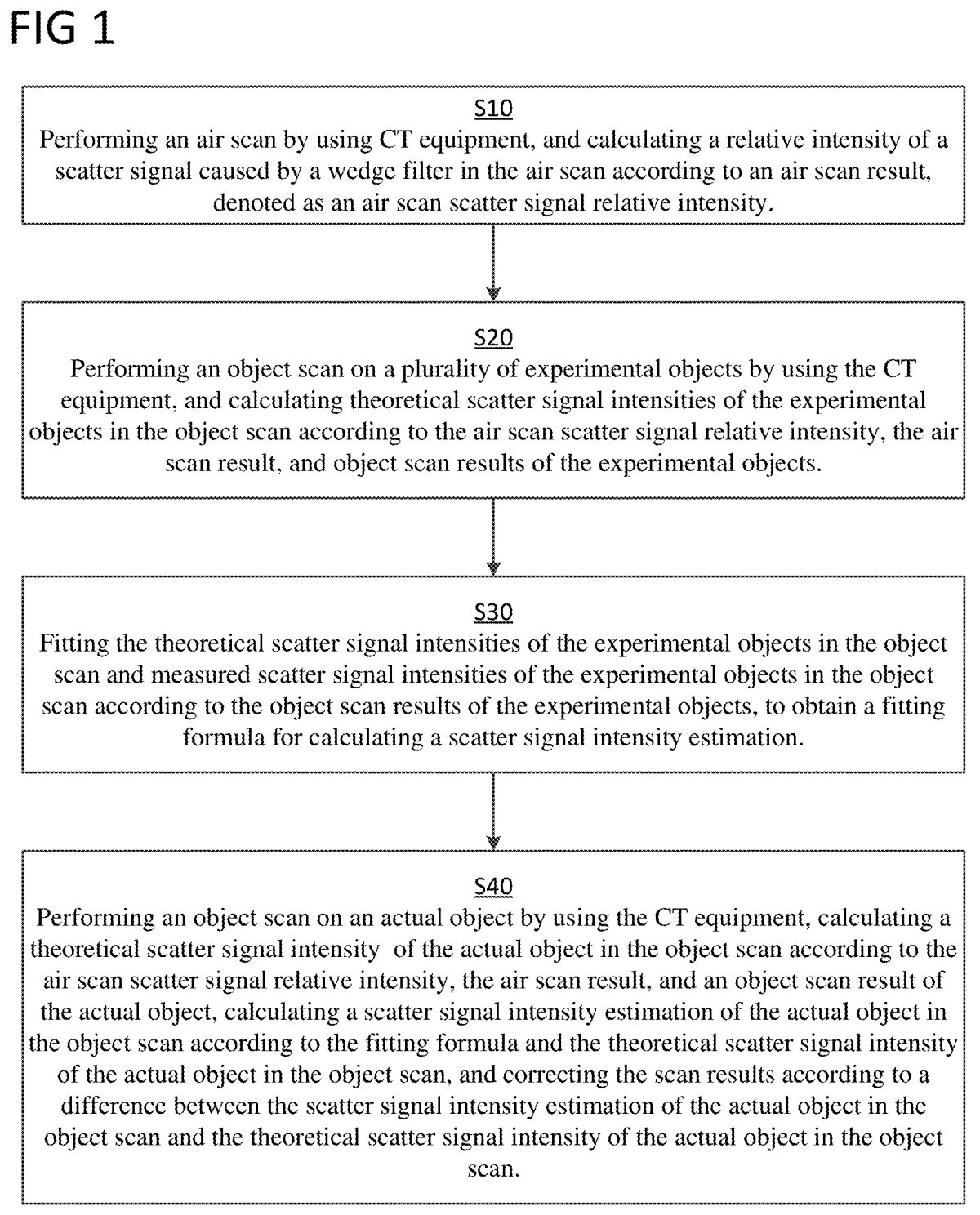

S10
Performing an air scan by using CT equipment, and calculating a relative intensity of a scatter signal caused by a wedge filter in the air scan according to an air scan result, denoted as an air scan scatter signal relative intensity.

---

S20
Performing an object scan on a plurality of experimental objects by using the CT equipment, and calculating theoretical scatter signal intensities of the experimental objects in the object scan according to the air scan scatter signal relative intensity, the air scan result, and object scan results of the experimental objects.

---

S30
Fitting the theoretical scatter signal intensities of the experimental objects in the object scan and measured scatter signal intensities of the experimental objects in the object scan according to the object scan results of the experimental objects, to obtain a fitting formula for calculating a scatter signal intensity estimation.

---

S40
Performing an object scan on an actual object by using the CT equipment, calculating a theoretical scatter signal intensity of the actual object in the object scan according to the air scan scatter signal relative intensity, the air scan result, and an object scan result of the actual object, calculating a scatter signal intensity estimation of the actual object in the object scan according to the fitting formula and the theoretical scatter signal intensity of the actual object in the object scan, and correcting the scan results according to a difference between the scatter signal intensity estimation of the actual object in the object scan and the theoretical scatter signal intensity of the actual object in the object scan.

FIG 2A

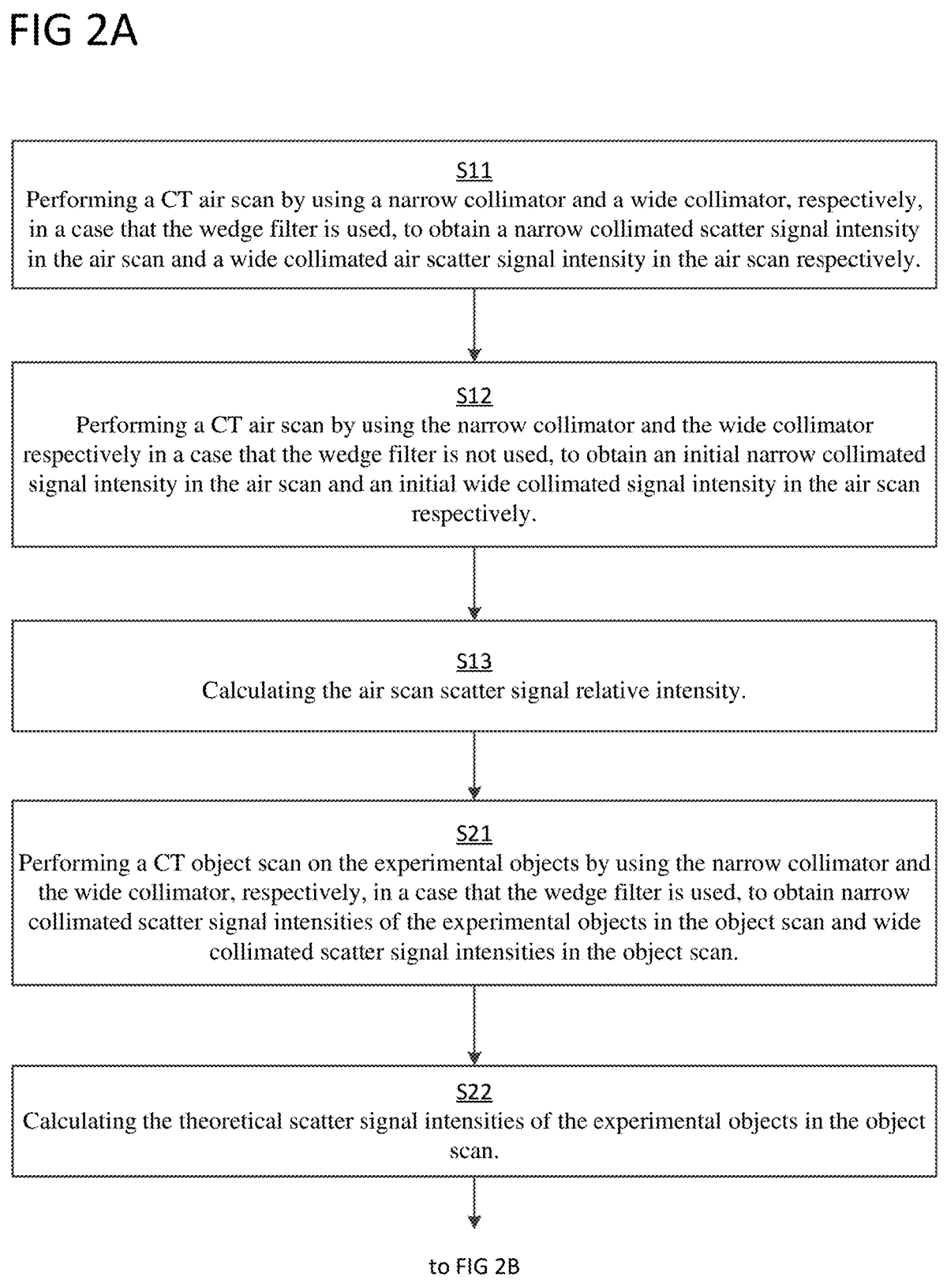

S11
Performing a CT air scan by using a narrow collimator and a wide collimator, respectively, in a case that the wedge filter is used, to obtain a narrow collimated scatter signal intensity in the air scan and a wide collimated air scatter signal intensity in the air scan respectively.

S12
Performing a CT air scan by using the narrow collimator and the wide collimator respectively in a case that the wedge filter is not used, to obtain an initial narrow collimated signal intensity in the air scan and an initial wide collimated signal intensity in the air scan respectively.

S13
Calculating the air scan scatter signal relative intensity.

S21
Performing a CT object scan on the experimental objects by using the narrow collimator and the wide collimator, respectively, in a case that the wedge filter is used, to obtain narrow collimated scatter signal intensities of the experimental objects in the object scan and wide collimated scatter signal intensities in the object scan.

S22
Calculating the theoretical scatter signal intensities of the experimental objects in the object scan.

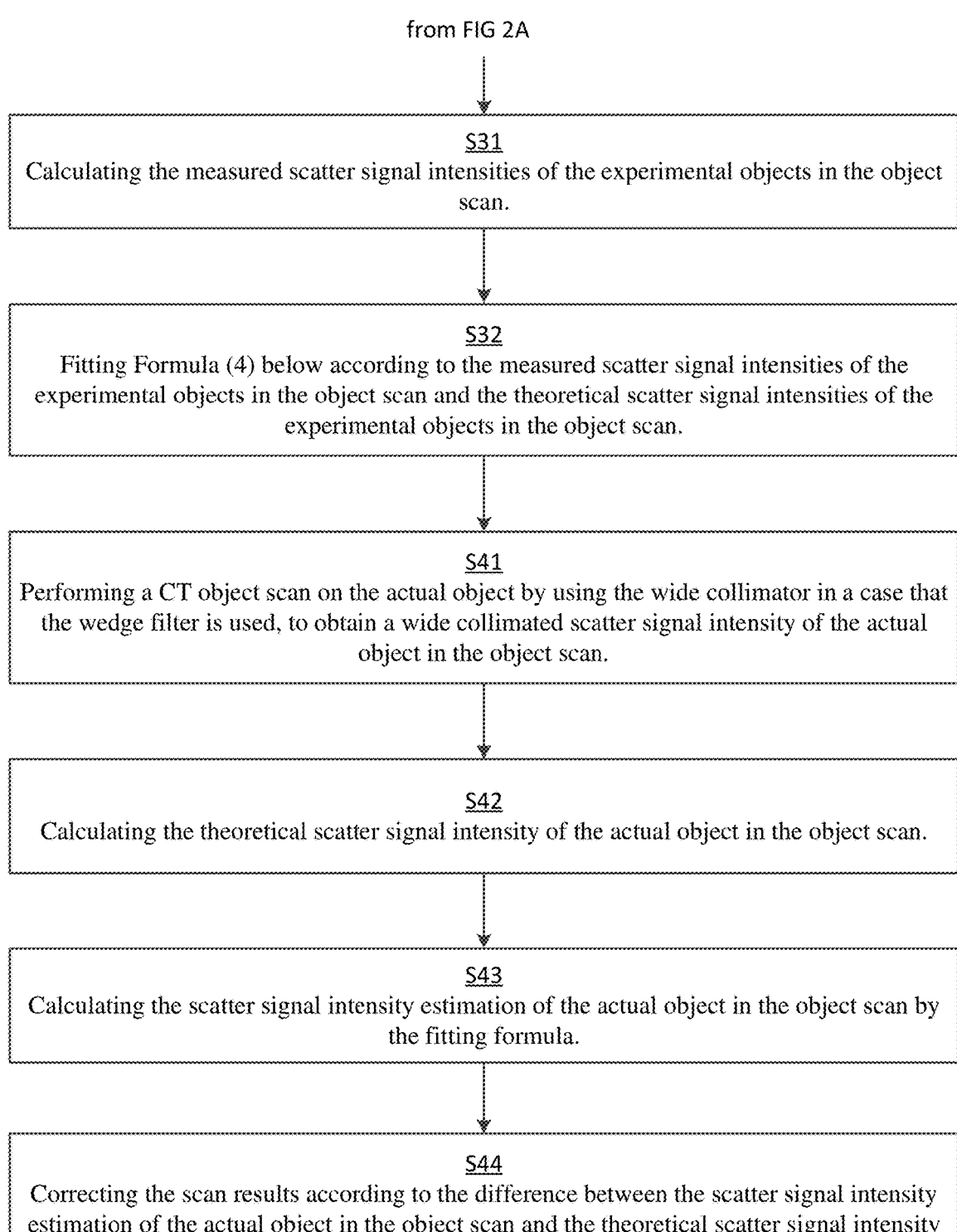

from FIG 2A

S31
Calculating the measured scatter signal intensities of the experimental objects in the object scan.

S32
Fitting Formula (4) below according to the measured scatter signal intensities of the experimental objects in the object scan and the theoretical scatter signal intensities of the experimental objects in the object scan.

S41
Performing a CT object scan on the actual object by using the wide collimator in a case that the wedge filter is used, to obtain a wide collimated scatter signal intensity of the actual object in the object scan.

S42
Calculating the theoretical scatter signal intensity of the actual object in the object scan.

S43
Calculating the scatter signal intensity estimation of the actual object in the object scan by the fitting formula.

S44
Correcting the scan results according to the difference between the scatter signal intensity estimation of the actual object in the object scan and the theoretical scatter signal intensity of the actual object in the object scan.

Channels

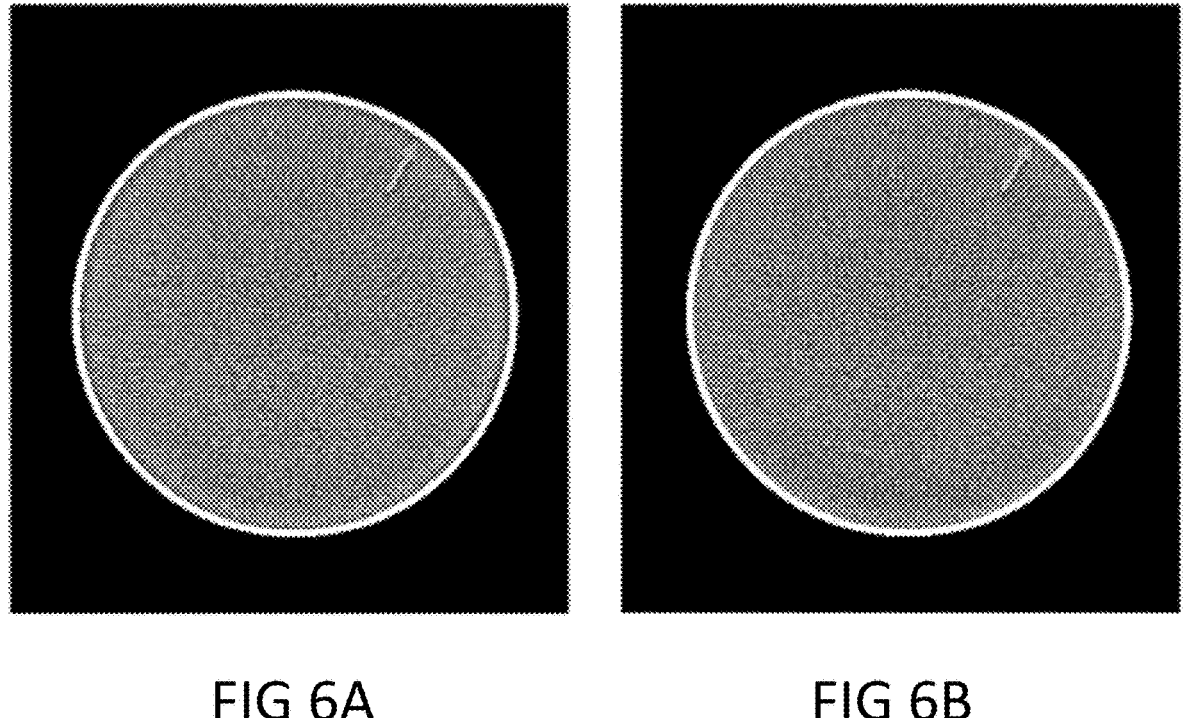
FIG 6A                    FIG 6B

CORRECTION METHOD FOR SCATTER SIGNAL CAUSED BY WEDGE FILTER

TECHNICAL FIELD

The present disclosure relates to a correction method, and in particular, to a method for correcting a scatter signal caused by a wedge filter in computed tomography (CT) equipment.

BACKGROUND

A wedge filter is an exceedingly common assembly in a CT system. The wedge filter may form a more even dose distribution in a patient. Because the wedge filter is a relatively strong attenuation object, the wedge filter generates scatter signals outside a scanned object. Although an air calibration can remove partial scatter signals caused by the wedge filter, some scatter signals remain in the scanned object.

At present, the scatter signals caused by the wedge filter may be removed through an anti-scatter grid or a computing model-based correction algorithm, which have strong scene dependence and need to be calibrated for each scene.

SUMMARY

An objective of the present disclosure is to provide a correction method for a scatter signal caused by a wedge filter, which can correct a scatter signal caused by a wedge filter more accurately.

The present disclosure further provides a storage medium, storing a correction program for a scatter signal caused by a wedge filter, where when the correction program is executed by a processor, the steps of the correction method for a scatter signal caused by a wedge filter are processed.

The present disclosure provides a correction method for a scatter signal caused by a wedge filter, including: S10: performing an air scan by using CT equipment, and calculating a relative intensity of a scatter signal caused by a wedge filter in the air scan according to an air scan result, denoted as an air scan scatter signal relative intensity $W_{air}$: S20: performing an object scan on a plurality of experimental objects by using the CT equipment, and calculating theoretical scatter signal intensities $W_{theo}$ of the experimental objects in the object scan according to the air scan scatter signal relative intensity $W_{air}$, the air scan result, and object scan results of the experimental objects: S30: fitting the theoretical scatter signal intensities $W_{theo}$ of the experimental objects in the object scan and measured scatter signal intensities $W_{meas}$ of the experimental objects in the object scan according to the object scan results of the experimental objects, to obtain a fitting formula for calculating a scatter signal intensity estimation $W_{act}$, and S40: performing an object scan on an actual object by using the CT equipment, calculating a theoretical scatter signal intensity $W_{theo}$ of the actual object in the object scan according to the air scan scatter signal relative intensity $W_{air}$, the air scan result, and an object scan result of the actual object, calculating a scatter signal intensity estimation $W_{act}$ of the actual object in the object scan according to the fitting formula and the theoretical scatter signal intensity $W_{theo}$ of the actual object in the object scan, and correcting the scan results according to a difference between the scatter signal intensity estimation $W_{act}$ of the actual object in the object scan and the theoretical scatter signal intensity $W_{theo}$ of the actual object in the object scan.

In the correction method for a scatter signal caused by a wedge filter provided by the present disclosure, air scan data is used as an input so that the estimation of a scatter signal caused by a wedge filter is more accurate. In addition, the method requires fewer algorithms and is also applicable to scans of clinical patients.

In another exemplary implementation of the correction method for a scatter signal caused by a wedge filter, step S10 includes: S11: performing a CT air scan by using a narrow collimator and a wide collimator, respectively, in a case that the wedge filter is used, to obtain a narrow collimated scatter signal intensity $I_{n\_air}$ in the air scan and a wide collimated air scatter signal intensity $I_{b\_air}$ in the air scan respectively: S12: performing a CT air scan by using the narrow collimator and the wide collimator respectively in a case that the wedge filter is not used, to obtain an initial narrow collimated signal intensity $I_{n\_p\_air}$ in the air scan and an initial wide collimated signal intensity $I_{b\_p\_air}$ in the air scan respectively: and S13: calculating the air scan scatter signal relative intensity $W_{air}$ by Formula (1) below:

$$W_{air} = (I_{b\_air} - I_{n\_air})/I_{b\_air} - (I_{b\_p\_air} - I_{n\_p\_air})/I_{b\_p\_air}. \qquad \text{Formula (1)}$$

The scatter signal in the air scan with the wedge filter is first obtained in S11, and then the scatter signal in the air scan with the wedge filter is removed in S12. The difference between the scatter signals obtained in S11 and S12 is calculated to obtain the relative intensity in S13. It is only in this case that the obtained signal can be considered as the scatter signal of only the wedge filter. The air scan scatter signal relative intensity obtained in S13 excludes the impact of different initial signal intensities caused by both the wide collimator and the narrow collimator.

In still another exemplary implementation of the correction method for a scatter signal caused by a wedge filter, step S20 includes: S21: performing a CT object scan on the experimental objects by using the narrow collimator and the wide collimator, respectively, in a case that the wedge filter is used, to obtain narrow collimated scatter signal intensities $I_{n\_obj}$ of the experimental objects in the object scan and wide collimated scatter signal intensities $I_{b\_obj}$ in the object scan, and S22: calculating the theoretical scatter signal intensities $W_{theo}$ of the experimental objects in the object scan by Formula (2) below: $W_{theo}=W_{air}*I_{b\_obj}/I_{b\_air}$ Formula (2). After air correction in step 10, the remaining amount of the scatter signals after passing through the experimental objects is calculated in step 20. Because the scattering caused by the experimental objects is not considered, the following steps S30 and S40 are performed.

In still another exemplary implementation of the correction method for a scatter signal caused by a wedge filter, step S30 includes: S31: calculating the measured scatter signal intensities $W_{meas}$ of the experimental objects in the object scan by Formula (3) below: $W_{meas}=I_{b\_obj}/I_{b\_air}-I_{n\_obj}/I_{n\_air}$, Formula (3): and S32: fitting Formula (4) below according to the measured scatter signal intensities $W_{meas}$ of the experimental objects in the object scan and the theoretical scatter signal intensities $W_{theo}$ of the experimental objects in the object scan, where the measured scatter signal intensities $W_{meas}$ of the experimental objects in the object scan are used as fit target values of scatter signal intensity estimations $W_{act}$ in the object scan, $W_{act}=p·W_{theo}*G$ Formula (4), where P is a scaling factor, and G is a Gaussian convolution kernel.

In still another exemplary implementation of the correction method for a scatter signal caused by a wedge filter, step

S40 includes: S41: performing a CT object scan on the actual object by using the wide collimator in a case that the wedge filter is used, to obtain a wide collimated scatter signal intensity $I_{b\_obj}$ of the actual object in the object scan, S42: calculating the theoretical scatter signal intensity $W_{theo}$ of the actual object in the object scan by Formula (2) according to the wide collimated scatter signal intensity $I_{b\_obj}$ of the actual object in the object scan, S43: calculating the scatter signal intensity estimation $W_{act}$ of the actual object in the object scan by the fitting formula, and S44: correcting the scan results according to the difference between the scatter signal intensity estimation $W_{act}$ of the actual object in the object scan and the theoretical scatter signal intensity $W_{theo}$ of the actual object in the object scan.

The narrow collimator and the wide collimator used in the present disclosure are both commonly used apparatuses in the CT equipment. The narrow collimator refers to a collimator with an aperture of 0.5 mm or less, and the wide collimator refers to a collimator with an aperture larger than that of the narrow collimator.

In still another exemplary implementation of the correction method for a scatter signal caused by a wedge filter, the experimental objects are CT water equivalent phantoms.

The present disclosure further provides a storage medium, storing a correction program for a scatter signal caused by a wedge filter, where when the correction program is executed by a processor, the step of the foregoing correction method is processed.

BRIEF DESCRIPTION OF THE DRAWINGS

The accompanying drawings below are only intended to provide exemplary descriptions and explanations for the present disclosure but are not intended to limit the scope of the present disclosure.

FIG. 1 is a flowchart of an exemplary implementation of a correction method for a scatter signal caused by a wedge filter;

FIGS. 2A and 2B are another flowchart of an exemplary implementation of a correction method for a scatter signal caused by a wedge filter;

FIG. 6A shows a reconstructed image of a CT water equivalent phantom with a diameter of 30 cm without being corrected by a method of the present disclosure; and FIG. 6B shows a reconstructed image of a CT water equivalent phantom with a diameter of 30 cm corrected by a method of the present disclosure.

DETAILED DESCRIPTION

Figure 3:
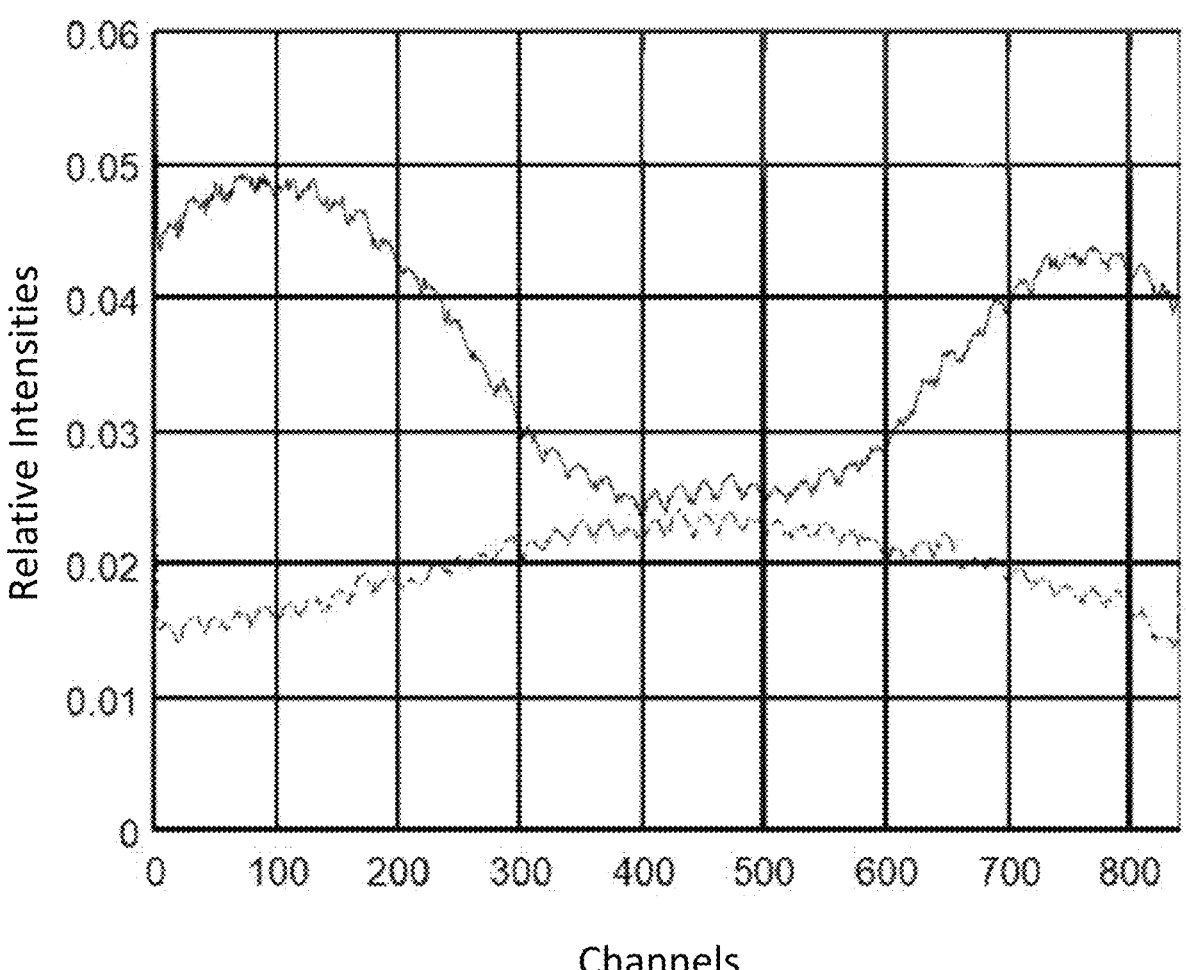
FIG. 3 shows a difference signal of an air scan obtained in step S11 and step S12, where a solid line represents a case of performing a CT air scan by using a narrow collimator and a wide collimator, respectively, in a case that a wedge filter is used, and a dotted line represents a case of performing a CT air scan by using the narrow collimator and the wide collimator respectively in a case that the wedge filter is not used.

To have a clearer understanding of the technical features, the objectives, and the effects of the aspects of the present disclosure, specific implementations of the aspects of the present disclosure are now illustrated with reference to the accompanying drawings. In the accompanying drawings, the same reference numerals represent components with the same structures or similar structures but the same functions.

In this specification, "exemplary" indicates "serving as an example, a case, or description," and any illustration or implementation described as "schematic" in this specification should not be interpreted as a more preferred or more advantageous technical solution.

For brevity of the accompanying drawings, only parts related to the present disclosure are schematically shown in the accompanying drawings and do not represent actual structures as products.

FIG. 1 is a flowchart of an exemplary implementation of a correction method for a scatter signal caused by a wedge filter. Referring to FIG. 1, the correction method for a scatter signal caused by a wedge filter includes the following steps.

S10: Perform an air scan by using CT equipment and calculate a relative intensity of a scatter signal caused by a wedge filter in the air scan according to an air scan result, denoted as an air scan scatter signal relative intensity $W_{air}$;

S20: Perform an object scan on a plurality of experimental objects by using the CT equipment, and calculate theoretical scatter signal intensities $W_{theo}$ of the experimental objects in the object scan according to the air scan scatter signal relative intensity $W_{air}$, the air scan result, and object scan results of the experimental objects, where the experimental objects may be CT water equivalent phantoms or human bodies.

S30: Fit the theoretical scatter signal intensities $W_{theo}$ of the experimental objects in the object scan and measured scatter signal intensities $W_{meas}$ of the experimental objects in the object scan according to the object scan results of the experimental objects, to obtain a fitting formula for calculating a scatter signal intensity estimation $W_{act}$, and

S40: Perform an object scan on an actual object by using the CT equipment, calculate a theoretical scatter signal intensity $W_{theo}$ of the actual object in the object scan according to the air scan scatter signal relative intensity $W_{air}$, the air scan result, and an object scan result of the actual object, calculate a scatter signal intensity estimation $W_{act}$ of the actual object in the object scan according to the fitting formula and the theoretical scatter signal intensity $W_{theo}$ of the actual object in the object scan, and correct the scan results according to a difference between the scatter signal intensity estimation $W_{act}$ of the actual object in the object scan and the theoretical scatter signal intensity $W_{theo}$ of the actual object in the object scan.

FIGS. 2A and 2B are another flowchart of an exemplary implementation of a correction method for a scatter signal caused by a wedge filter. Referring to FIGS. 2A and 2B, the correction method for a scatter signal caused by a wedge filter includes the following steps.

S11: Perform a CT air scan by using a narrow collimator and a wide collimator, respectively, in a case that the wedge filter is used, to obtain a narrow collimated scatter signal intensity $I_{n\_air}$ in the air scan and a wide collimated air scatter signal intensity $I_{b\_air}$ in the air scan respectively.

S12: Perform a CT air scan by using the narrow collimator and the wide collimator, respectively, in a case that the wedge filter is not used, to obtain an initial narrow collimated signal intensity $I_{n\_p\_air}$ in the air scan and an initial wide collimated signal intensity $I_{b\_p\_air}$ in the air scan respectively. FIG. 3 shows a difference signal of air scattering obtained in step S11 and step S12, where a solid line represents a case of performing a CT air scan by using a narrow collimator and a wide collimator, respectively, in a case that a wedge filter is used, and a dotted line represents a case of performing a CT air scan by using the narrow collimator and the wide collimator respectively in a case that the wedge filter is not used.

S13: Calculate the air scan scatter signal relative intensity $W_{air}$ by Formula (1) below:

$$W_{air} = (I_{b\_air} - I_{n\_air})/I_{b\_air} - (I_{b\_p\_air} - I_{n\_p\_air})/I_{b\_p\_air}. \qquad \text{Formula (1)}$$

Figure 4:
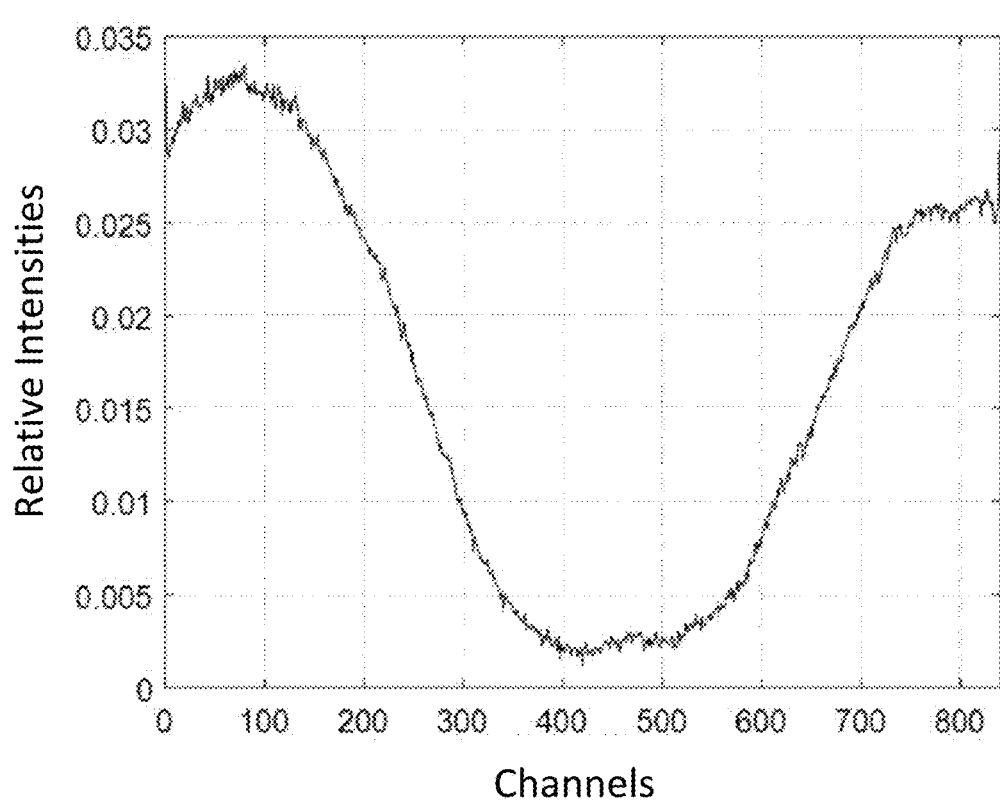
FIG. 4 shows an air scan scatter signal relative intensity $W_{air}$ obtained in step S13 in an exemplary implementation of a correction method for a scatter signal caused by a wedge filter.
Figure 5:
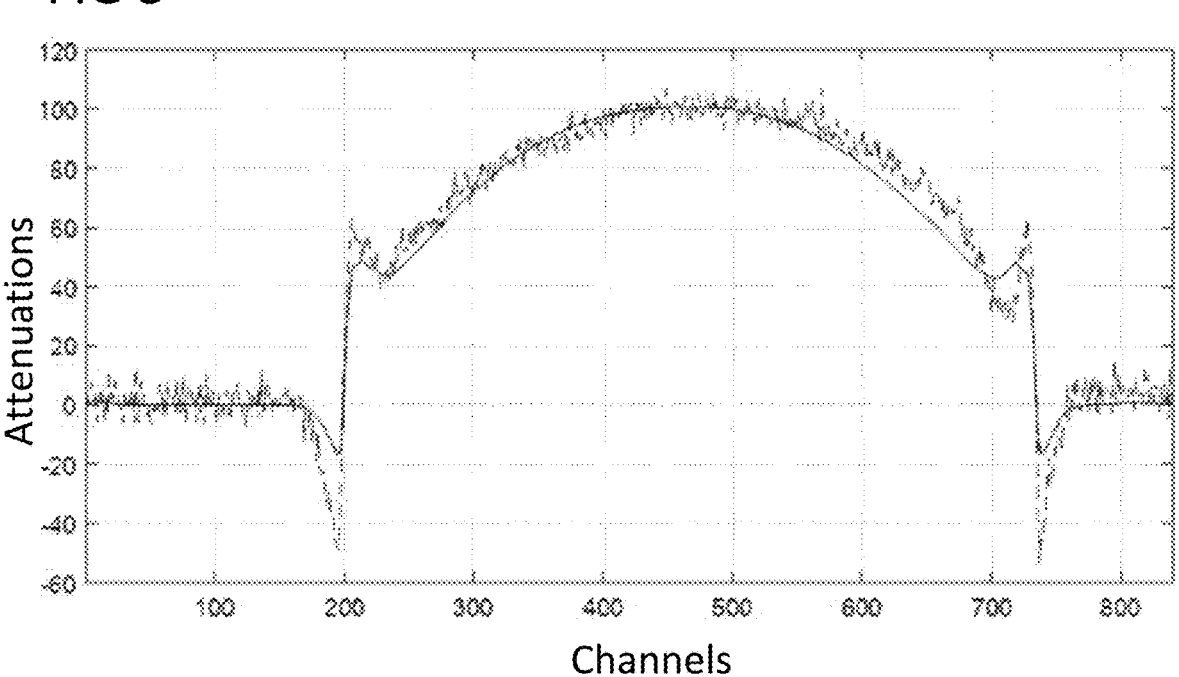
FIG. 5 shows a fitting process of S32 in an exemplary implementation of a correction method for a scatter signal caused by a wedge filter, where a dotted line shows measured scatter signal intensities $W_{meas}$ of experimental objects in an object scan, and a solid line shows scatter signal intensity estimations $W_{act}$ of the experimental objects in the object scan.

FIG. 4 shows an air scan scatter signal relative intensity $W_{air}$ obtained by subtracting curves in FIG. 3.

S21: Perform a CT object scan on the experimental objects by using the narrow collimator and the wide collimator, respectively, in a case that the wedge filter is used, to obtain narrow collimated scatter signal intensities $I_{n\_obj}$ of the experimental objects in the object scan and wide collimated scatter signal intensities $I_{b\_obj}$ in the object scan.

S22: Calculate the theoretical scatter signal intensities $W_{theo}$ of the experimental objects in the object scan by Formula (2) below:

$$W_{theo} = W_{air} * I_{b\_obj}/I_{b\_air}. \qquad \text{Formula (2)}$$

S31: Calculate the measured scatter signal intensities $W_{meas}$ of the experimental objects in the object scan by Formula (3) below:

$$W_{meas} = I_{b\_obj}/I_{b\_air} - I_{n\_obj}/I_{n\_air}. \qquad \text{Formula (3)}$$

S32: Fit Formula (4) below according to the measured scatter signal intensities $W_{meas}$ of the experimental objects in the object scan and the theoretical scatter signal intensities $W_{theo}$ of the experimental objects in the object scan, where the measured scatter signal intensities $W_{meas}$ of the experimental objects in the object scan are used as fit target values of scatter signal intensity estimations $W_{act}$ in the object scan, $W_{act} = p \cdot W_{theo} * G$ Formula (4), where P is a scaling factor, and G is a Gaussian convolution kernel.

S41: Perform a CT object scan on the actual object by using the wide collimator in a case that the wedge filter is used, to obtain a wide collimated scatter signal intensity $I_{b\_obj}$ of the actual object in the object scan.

S42: Calculate the theoretical scatter signal intensity $W_{theo}$ of the actual object in the object scan by Formula (2) according to the wide collimated scatter signal intensity $I_{b\_obj}$ of the actual object in the object scan.

S43: Calculate the scatter signal intensity estimation $W_{act}$ of the actual object in the object scan by the fitting formula.

S44: Correct the scan results according to the difference between the scatter signal intensity estimation $W_{act}$ of the actual object in the object scan and the theoretical scatter signal intensity $W_{theo}$ of the actual object in the object scan.

FIG. 6A shows a reconstructed image of a CT water equivalent phantom with a diameter of 30 cm without being corrected by a method of the present disclosure. FIG. 6B shows a reconstructed image of a CT water equivalent phantom with a diameter of 30 cm corrected by a method of the present disclosure. It can be seen that an area indicated by an arrow shows that the reconstructed image of the CT water equivalent phantom with a diameter of 30 cm without being corrected by the method of the present disclosure has darker shade, while the reconstructed image of the CT water equivalent phantom with a diameter of 30 cm corrected by the method of the present disclosure has lighter shade.

Through the descriptions of the foregoing implementations, a person skilled in the art may clearly understand that the methods in the foregoing aspects may be implemented by means of software and a necessary general hardware platform and, certainly, may be implemented by hardware, but in many cases, the former manner is a better implementation. Based on such an understanding, the technical solutions of the present disclosure or the part that makes contributions to the prior art may be substantially embodied in the form of a software product. The computer software product is stored in a storage medium (such as a ROM/RAM, a magnetic disk, and an optical disc) and contains several instructions to enable a terminal device (which may be a mobile phone, a computer, a server, an air conditioner or a network device) to perform the method according to the aspects of the present disclosure.

A series of detailed descriptions listed above are only specific descriptions of the feasible aspects of the present disclosure, which are not intended to limit the protection scope of the present disclosure. Any equivalent implementation solution or transformation without departing from the technical spirit of the present disclosure, such as combination, division, or repetition of features, shall fall within the protection scope of the present disclosure.

The invention claimed is:

1. A correction method for a scatter signal caused by a wedge filter, comprising:

S10: performing an air scan by using computed tomography (CT) equipment, and calculating a relative intensity of a scatter signal caused by a wedge filter in the air scan according to an air scan result, denoted as an air scan scatter signal relative intensity $W_{air}$;

S20: performing an object scan on a plurality of experimental objects by using the CT equipment, and calculating theoretical scatter signal intensities $W_{theo}$ of the experimental objects in the object scan according to the air scan scatter signal relative intensity $W_{air}$, the air scan result, and object scan results of the experimental objects;

S30: fitting the theoretical scatter signal intensities $W_{theo}$ of the experimental objects in the object scan and measured scatter signal intensities $W_{meas}$ of the experimental objects in the object scan according to the object scan results of the experimental objects, to obtain a fitting formula for calculating a scatter signal intensity estimation $W_{act}$; and S40: performing an object scan on an actual object by using the CT equipment, calculating a theoretical scatter signal intensity $W_{theo}$ of the actual object in the object scan according to the air scan scatter signal relative intensity $W_{air}$, the air scan result, and an object scan result of the actual object, calculating a scatter signal intensity estimation $W_{act}$ of the actual object in the object scan according to the fitting formula and the theoretical scatter signal intensity $W_{theo}$ of the actual object in the object scan, and correcting the scan results according to a difference between the scatter signal intensity estimation $W_{act}$ of the actual object in the object scan and the theoretical scatter signal intensity $W_{theo}$ of the actual object in the object scan.

2. The correction method for a scatter signal caused by a wedge filter according to claim 1, wherein the step S10 comprises:

S11: performing a CT air scan by using a narrow collimator and a wide collimator respectively in a case that the wedge filter is used, to obtain a narrow collimated scatter signal intensity $I_{n\_air}$ in the air scan and a wide collimated air scatter signal intensity $I_{b\_air}$ in the air scan respectively;

S12: performing a CT air scan by using the narrow collimator and the wide collimator respectively in a case that the wedge filter is not used, to obtain an initial narrow collimated signal intensity $I_{n\_p\_air}$ in the air scan and an initial wide collimated signal intensity $I_{b\_p\_air}$ in the air scan respectively; and S13: calculating the air scan scatter signal relative intensity $W_{air}$ by Formula (1) below:

$$W_{air} = (I_{b\_air} - I_{n\_air})/I_{b\_air} - (I_{b\_p\_air} - I_{n\_p\_air})/I_{b\_p\_air}.$$

3. The correction method for a scatter signal caused by a wedge filter according to claim 2, wherein the step S20 comprises:

S21: performing a CT object scan on the experimental objects by using the narrow collimator and the wide collimator respectively in a case that the wedge filter is used, to obtain narrow collimated scatter signal intensities $I_{n\_obj}$ of the experimental objects in the object scan and wide collimated scatter signal intensities $I_{b\_obj}$ in the object scan; and S22: calculating the theoretical scatter signal intensities $W_{theo}$ of the experimental objects in the object scan by Formula (2) below:

$$W_{theo} = W_{air} * I_{b\_obj}/I_{b\_air}.$$

4. The correction method for a scatter signal caused by a wedge filter according to claim 3, wherein the step S30 comprises:

S31: calculating the measured scatter signal intensities $W_{meas}$ of the experimental objects in the object scan by Formula (3) below:

$$W_{meas} = I_{b\_obj}/I_{b\_air} - I_{n\_obj}/I_{n\_air};\ \text{and}$$

S32: fitting Formula (4) below according to the measured scatter signal intensities $W_{meas}$ of the experimental objects in the object scan and the theoretical scatter signal intensities $W_{theo}$ of the experimental objects in the object scan, wherein the measured scatter signal intensities $W_{meas}$ of the experimental objects in the object scan are used as fit target values of scatter signal intensity estimations $W_{act}$ in the object scan, $$W_{act} = p \cdot W_{theo} * G,$$

wherein P is a scaling factor, and G is a Gaussian convolution kernel.

5. The correction method for a scatter signal caused by a wedge filter according to claim 4, wherein the step S40 comprises:

S41: performing a CT object scan on the actual object by using the wide collimator in a case that the wedge filter is used, to obtain a wide collimated scatter signal intensity $I_{b\_obj}$ of the actual object in the object scan;

S42: calculating the theoretical scatter signal intensity $W_{theo}$ of the actual object in the object scan by Formula (2) according to the wide collimated scatter signal intensity $I_{b\_obj}$ of the actual object in the object scan;

S43: calculating the scatter signal intensity estimation $W_{act}$ of the actual object in the object scan by the fitting formula; and S44: correcting the scan results according to the difference between the scatter signal intensity estimation $W_{act}$ of the actual object in the object scan and the theoretical scatter signal intensity $W_{theo}$ of the actual object in the object scan.

6. The correction method for a scatter signal caused by a wedge filter according to claim 1, wherein the experimental objects are CT water equivalent phantoms.

7. A non-transitory storage medium, storing a correction program for a scatter signal caused by a wedge filter, wherein when the correction program is executed by a processor, the steps of the correction method according to claim 1 are processed.

\* \* \* \* \*